(12) United States Patent
Bornhoft et al.

(10) Patent No.: US 7,418,297 B2
(45) Date of Patent: Aug. 26, 2008

(54) FRAME LENGTH MODULATION AND PULSE POSITION MODULATION SYSTEM

(75) Inventors: Reid Bornhoft, Lino Lakes, MN (US); Brian P. Brockway, Shoreview, MN (US); Matt Kunz, White Bear Lake, MN (US); Gregg Lichtscheidl, Roseville, MN (US); Brock Lindstedt, Shoreview, MN (US); Perry A. Mills, Arden Hills, MN (US)

(73) Assignee: Transoma Medical, Inc., St. Paul, MN (US)

( * ) Notice: Subject to any disclaimer, the term of this patent is extended or adjusted under 35 U.S.C. 154(b) by 330 days.

(21) Appl. No.: 11/193,818

(22) Filed: Jul. 28, 2005

(65) Prior Publication Data

US 2005/0261749 A1  Nov. 24, 2005

Related U.S. Application Data (62) Division of application No. 09/968,644, filed on Oct. 1, 2001, now Pat. No. 6,947,795.

(51) Int. Cl.
H03K 9/041 (2006.01)

(52) U.S. Cl. .......................... 607/60; 607/32; 375/238; 375/239

(58) Field of Classification Search ............. 607/30–32, 607/59, 60; 128/903; 375/238, 239
See application file for complete search history.

(56) References Cited

U.S. PATENT DOCUMENTS

| | | | |
|---|---|---|---|
| 4,281,664 A | 8/1981 | Duggan | |
| 4,374,382 A | 2/1983 | Markowitz | |
| 4,513,403 A | 4/1985 | Troy | |
| 4,531,523 A | 7/1985 | Anderson | |
| 4,556,063 A | 12/1985 | Thompson et al. | |
| RE32,361 E | 2/1987 | Duggan | |
| 5,107,833 A | 4/1992 | Barsness | |
| 5,127,404 A | 7/1992 | Wyborny et al. | |
| 5,137,022 A | 8/1992 | Henry | |
| 5,168,871 A | 12/1992 | Grevious | |

(Continued)

FOREIGN PATENT DOCUMENTS

DE 3816018 11/1988

(Continued)

*Primary Examiner*—Carl H. Layno
*Assistant Examiner*—Yun Haeng Lee
(74) *Attorney, Agent, or Firm*—Fish & Richardson P.C.

(57) ABSTRACT

A system includes a transceiver circuit to transceive at least a first analog signal and a digital signal. The system also includes a controller circuit, coupled to the transceiver circuit, to deliver at least one control signal thereto, the controller circuit including executable instructions defining a data frame for communication of the first analog signal and the digital signal, endpoints of the data frame defined by portions of successive first and second synchronization signals and defining a corresponding frame interval, the data frame including a first data band for transceiving a first data pulse therein. A relative position in time of the first data pulse represents the first analog signal, and a modulation of the frame interval represents the digital signal. The system further includes an analog signal interface circuit, coupled to the transceiver circuit, to provide at least the first analog signal representative of acquired data.

21 Claims, 6 Drawing Sheets

U.S. PATENT DOCUMENTS

| | | |
|---|---|---|
| 5,241,961 A | 9/1993 | Henry |
| 5,292,343 A | 3/1994 | Blanchette et al. |
| 5,314,450 A | 5/1994 | Thompson |
| 5,324,315 A | 6/1994 | Grevious |
| 5,330,513 A | 7/1994 | Nichols et al. |
| 5,350,411 A | 9/1994 | Ryan et al. |
| 5,354,319 A | 10/1994 | Wyborny et al. |
| 5,383,909 A | 1/1995 | Keimel |
| 5,402,794 A | 4/1995 | Wahlstrand et al. |
| 5,411,536 A | 5/1995 | Armstrong |
| 5,522,866 A | 6/1996 | Fernald |
| 5,611,346 A | 3/1997 | Heikkila et al. |
| 5,620,472 A | 4/1997 | Rahbari |
| 5,684,871 A | 11/1997 | Devon et al. |
| 5,752,976 A | 5/1998 | Duffin et al. |
| 5,752,977 A | 5/1998 | Grevious et al. |
| 5,766,232 A | 6/1998 | Grevious et al. |
| 5,782,890 A | 7/1998 | Wahlstrand et al. |
| 5,861,019 A | 1/1999 | Sun et al. |
| 5,899,931 A | 5/1999 | Deschamp et al. |
| 5,919,214 A | 7/1999 | Ciciarelli et al. |
| 5,999,857 A | 12/1999 | Weijand et al. |
| 6,009,350 A | 12/1999 | Renken |
| 6,083,248 A | 7/2000 | Thompson |
| 6,115,636 A | 9/2000 | Ryan |
| 6,167,310 A | 12/2000 | Grevious |
| 6,167,312 A | 12/2000 | Goedeke |
| 6,169,925 B1 | 1/2001 | Villaseca et al. |
| 6,201,993 B1 | 3/2001 | Kruse et al. |

FOREIGN PATENT DOCUMENTS

| | | |
|---|---|---|
| EP | 268 972 | 6/1988 |
| WO | WO 94/28968 | 12/1994 |

FRAME LENGTH MODULATION AND PULSE POSITION MODULATION SYSTEM

TECHNICAL FIELD

This document relates generally to communication systems and particularly, but not by way of limitation, to a system and method for telemetry of analog and digital data, such as between implantable and remote devices.

BACKGROUND

Electronic devices are often implanted within a human or animal for acquiring biological data or for providing therapy. It is often desirable for such an implanted device to wirelessly communicate with a remote external device. For example, the implanted device may communicate the acquired biological data to the remote device for processing and/or display or other user output. In another example, the implanted device may communicate to the remote device information about how the implanted device is configured. In a further example, the external device may communicate to the implanted device instructions for performing subsequent operations. Because the implanted device is often battery-powered, there is a need for the communication protocol to operate without consuming excessive energy, which would deplete the battery and, therefore, shorten the usable life of the implanted device. However, such low-power communication techniques may be particularly sensitive to environmental noise. Such noise can disrupt the data communication and can even corrupt the data being transmitted. Therefore, there is also a need for a low-power communication protocol that allows any such detected noise to be evaluated to determine whether the data being transmitted risks being corrupted.

SUMMARY

This document discusses a system and method that involves transceiving successive first and second synchronization signals defining endpoints of a frame. A digital signal is transceived by a modulating time interval between portions of the first and second synchronization signals. A first data pulse is transceived during the frame. A relative position in the frame of the first data pulse represents a first analog signal. The system and method discussed herein is particularly suited for the low-power transceiving of analog biological data from an implantable device to an external or other remote device. A further example permits noise and/or signal strength manifested during such communication to be quantified and evaluated, such as to qualify the data being transceived. Other aspects of the invention will be apparent on reading the following detailed description of the invention and viewing the drawings that form a part thereof.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

In this document, the terms "transceive," "transceiving," and "transceiver" refer to transmitting and/or receiving data. That is, these terms include all of: (1) transmitting, but not receiving; (2) receiving, but not transmitting; and, (3) both transmitting and receiving.

Figure 1:
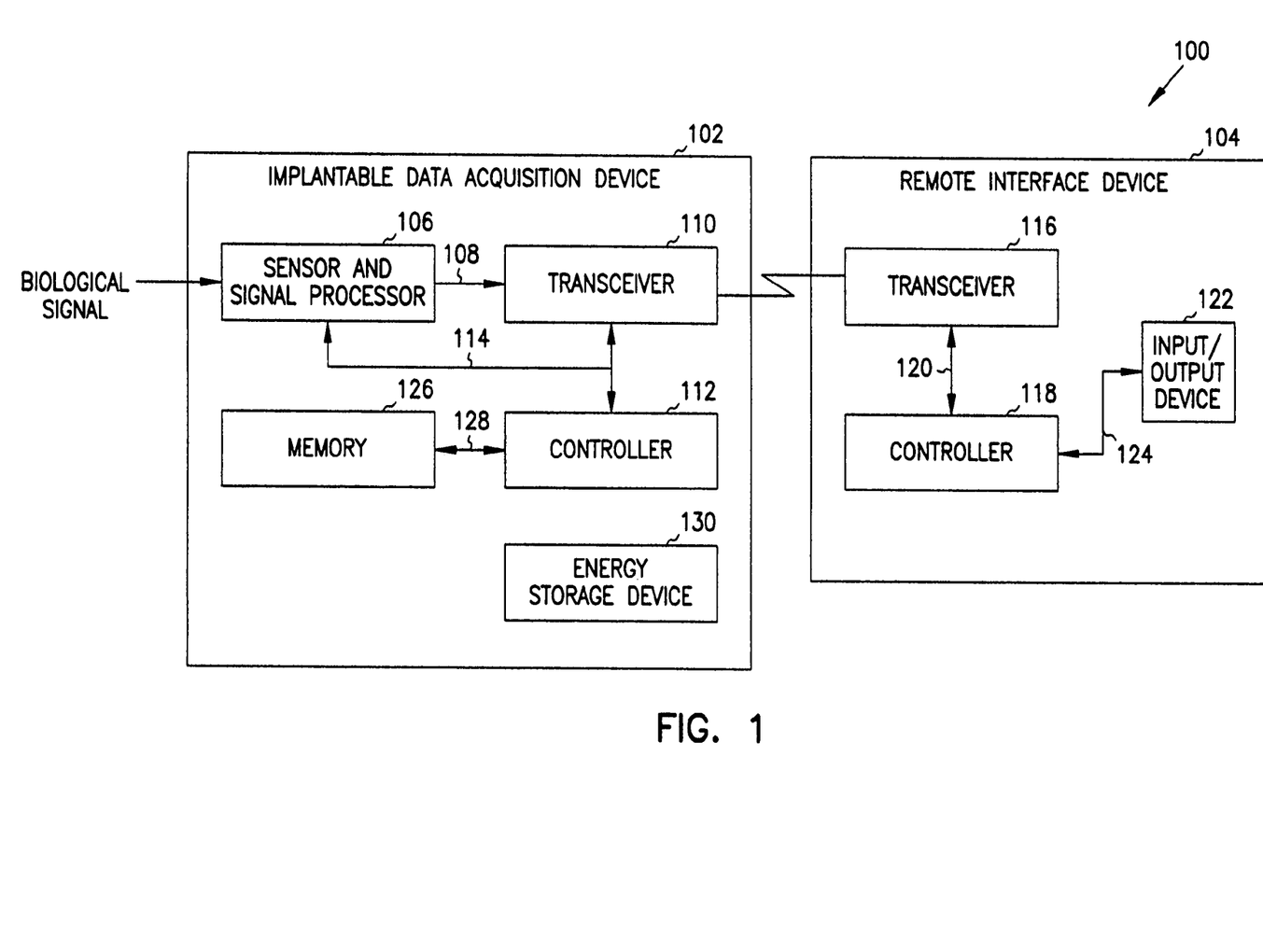
FIG. 1 is a block diagram illustrating generally one example of a system for acquiring and/or processing biological data received from a human or animal subject.

FIG. 1 is a block diagram illustrating generally one example of a system 100 for acquiring and/or processing biological data received from a human or animal subject. This example includes an implantable data acquisition device 102 configured for wireless communication with a remote interface device 104. The wireless communication is carried out using electromagnetic signals, such as short bursts of radio-frequency (RF) energy, referred to as pulses. In FIG. 1, implantable device 102 includes at least one sensor and signal processor circuit 106 that detects a biological signal received from the subject. Suitable sensor devices include, by way of example, but not by way of limitation, a biopotential sensor, a biofluid pressure sensor, a biofluid flow sensor, a temperature sensor, a tissue or other impedance sensor, a pH sensor, or an electrochemical sensor (e.g., to detect chemical messengers such as dopamine or metabolic substances such as oxygen). Sensor and signal processor 106 outputs at a node/bus 108 to a transceiver circuit 110 a signal representative of the detected biological signal. A controller circuit 112 is coupled at node/bus 114 to one or both of transceiver 110 and sensor and signal processor 106. Controller 112 is capable of sequencing through various control states such as, for example, by using a digital microprocessor having executable instructions stored in an associated instruction memory circuit, a microsequencer, or a state machine. In operation, by execution of these instructions, controller 112 provides control signals to transceiver 110 and/or sensor and signal processor 106 for controlling and timing their operation. In this example, device 102 also includes an electrically erasable and programmable read-only memory (EEPROM) or other non-volatile or volatile memory 126 coupled, at node/bus 128, to controller 112. Device 102 also includes a power source or energy storage device 130, such as a single-use or rechargeable battery and/or a reactive element such as a capacitor to store energy received from an external power source.

Remote device 104 (which may also be implanted in the human or animal subject or which is instead located external to the subject) includes a transceiver circuit 116 that is communicatively couplable to transceiver 110 of implantable device 102. Remote device 104 also includes a controller circuit 118, which is coupled to transceiver 116 via node/bus 120, and which is coupled to a user input/output (I/O) device 122 via node/bus 124. Controller 118 is capable of sequencing through various control states such as, for example, by using a digital microprocessor having executable instructions stored in an associated instruction memory circuit, a microsequencer, or a state machine. In operation, by execution of these instructions, controller 118 provides control signals to transceiver 116 and/or I/O device 122 for controlling and timing their operation.

Figure 2:
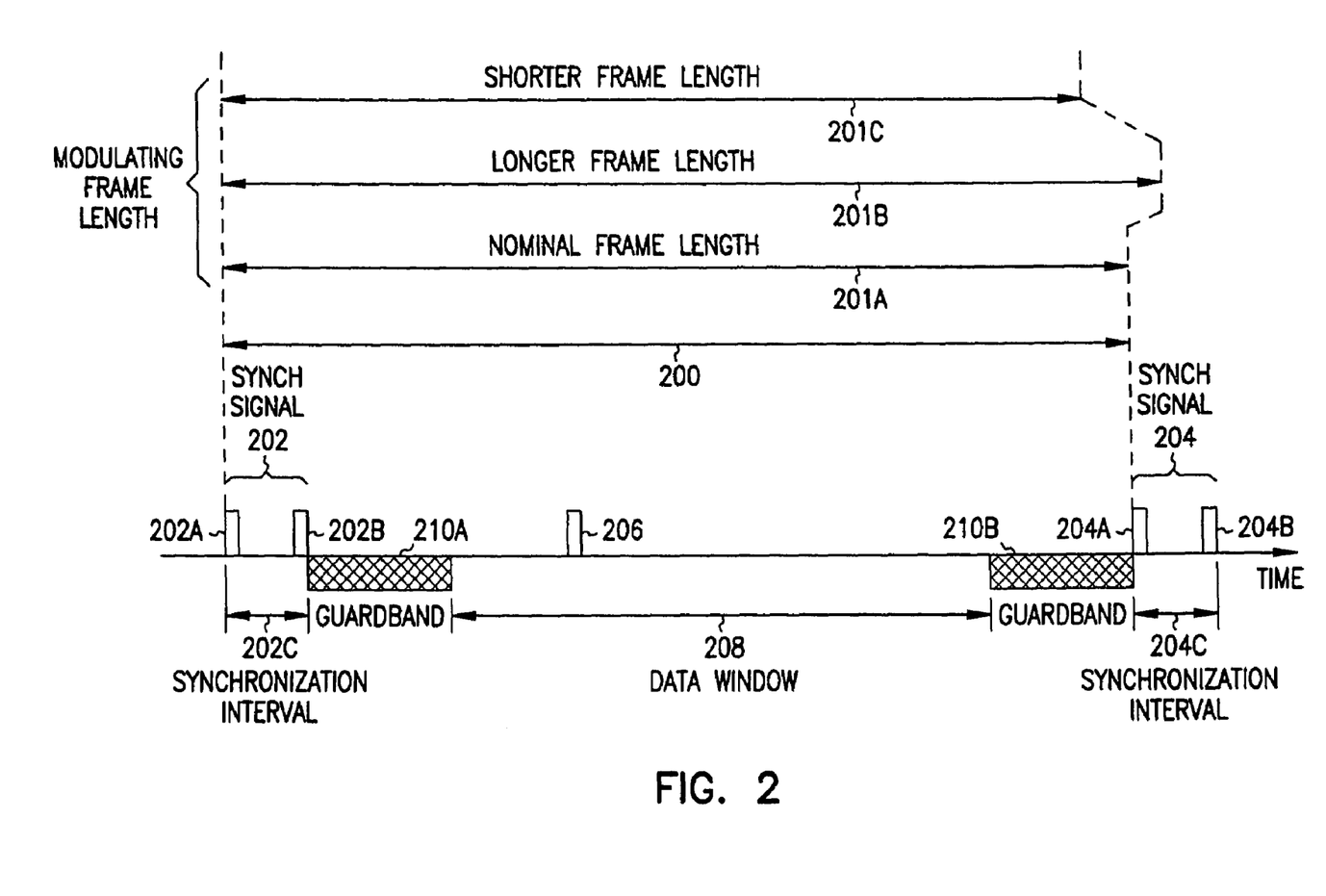
FIG. 2 is a timing diagram illustrating generally one example of a communication protocol.

In one example, implantable device 102 is configured to transmit both analog and digital information to be received by remote device 104. Controller 112 times the transmission of data pulses by transceiver 110, and controller 118 interprets the reception of these data pulses by transceiver 116 according to a predefined communication protocol. FIG. 2 is a timing diagram illustrating generally one example of such a communication protocol. FIG. 2 illustrates one frame 200 of data (having a variable frame length, as illustrated by 201A-C). Data is typically communicated over a plurality of successive such frames 200A, 200B, . . . , 200N. Frame 200 includes endpoints defined by a starting synchronization signal 202 and an ending synchronization signal 204. In this example, starting synchronization signal 202 includes at its endpoints identifiable symbols such as, for example, synchronization pulses 202A-B. Similarly, ending synchronization signal 204 includes at its endpoints identifiable symbols such as, for example, synchronization pulses 204A-B. The data communication "pulses" 202A-B and 204A-B are, in this example, more particularly described as short bursts of radio frequency (RF) energy, however, any other suitable detectable symbol could alternatively be used (e.g., infrared (IR) or other light or electromagnetic energy, inductive or magnetic-field coupling, electric field coupling, ultrasound or other pressure transmission, thermal energy transmission, or current wirelessly conducted through a patient's body, etc.). By way of example, but not by way of limitation, one pulse uses a 10-50 microsecond long burst of approximately 455 kHz energy. The time interval between synchronization pulses 202A-B, inclusive, is referred to as a synchronization interval 202C. Similarly, the time interval between synchronization pulses 204A-B, inclusive, is referred to as synchronization interval 204C.

FIG. 2 also illustrates a pulse-position-modulated (PPM) data pulse 206. The position at which data pulse 206 is transmitted within a "continuum" in data band or data window 208 encodes an analog signal. In one example, the analog signal is encoded by taking a relative position of data pulse 206 to one of the synchronization pulses 202A-B, which are issued synchronously to an underlying 32.768 kHz clock. One technique for encoding the analog signal is to charge a capacitor to a voltage that is representative of the analog signal and, upon issuance of the one of the synchronization pulses 202A-B, relative to which the position of data pulse 206 is measured, a constant current source begins discharging the capacitor. An analog comparator compares the capacitor voltage to a threshold voltage. When the capacitor voltage decreases to the threshold voltage, the comparator triggers issuance of data pulse 206.

Similarly, the relative position at which data pulse 206 is received within data window 208 decodes the analog signal. In one example, the analog signal encoded, communicated, and decoded is a signal representative of the detected biological signal, as discussed above. Moreover, as illustrated in FIG. 2, the duration of frame 200 is also modulated to encode digital data. In one example, the modulated length of frame 200 encodes a bit of digital data by selecting the particular length from three discrete values: (1) nominal/intermediate frame length 201A, which represents no change in the digital data from the preceding frame; (2) longer (e.g., adding one additional 32.768 kHz clock period) frame length 201B, which represents a transition from a "0" during the preceding frame to a "1" during the present frame; and (3) shorter (e.g., subtracting one 32.768 kHz clock period) frame length 201C, which represents a transition from a "1" during the preceding frame to a "0" during the present frame. Among other things, this encoding technique maintains, over the long-term, a fixed frame length, i.e., the cumulative deviation from the nominal frame length over does not exceed a single 32.768 kHz clock period from the nominal frame length value.

FIG. 2 also illustrates an example in which data window 208 is separated from synchronization signals 202 and 204 by respective guardbands 210A-B during which no data pulse(s) are communicated. Each of guardbands 210A-B has a duration that exceeds that of synchronization intervals 202C and 204C. Moreover, at least one of guardbands 210A-B has a duration that exceeds that of synchronization intervals 202C and 204C by a margin amount that is sufficient to accommodate the modulation of the length of frame 200.

Figure 3:
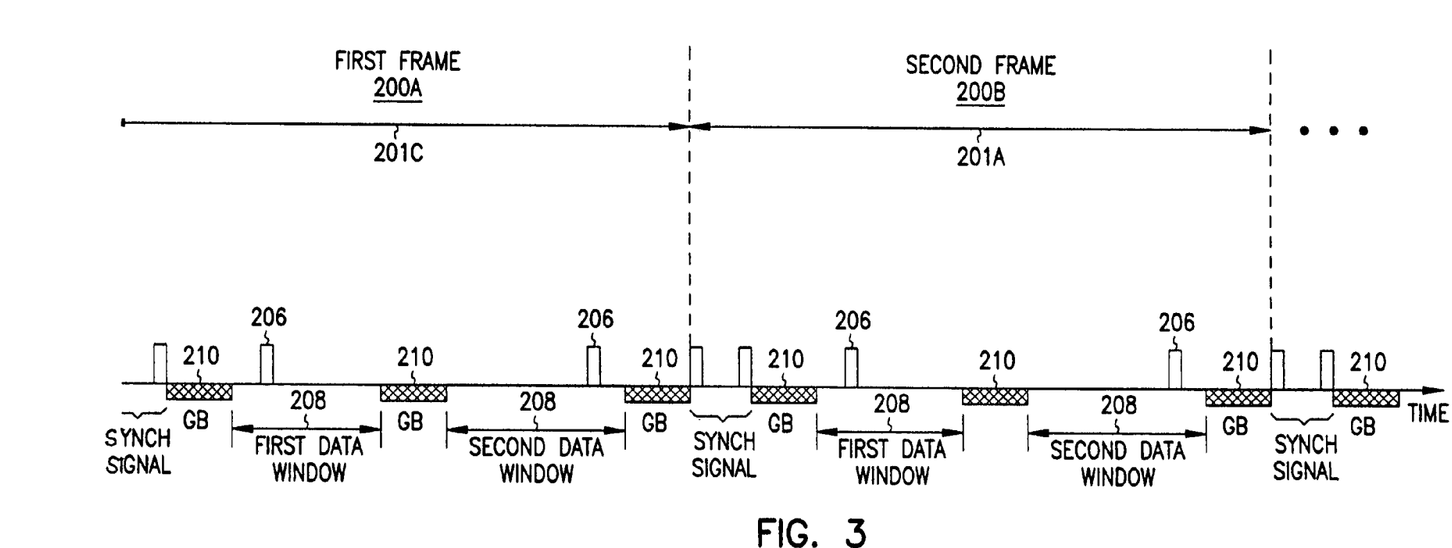
FIG. 3 is a timing diagram illustrating a further example in which each frame includes more than one data band or data window in which a corresponding data pulse communicates a pulse position modulation (PPM) encoded analog signal.

FIG. 3 is a timing diagram illustrating a further example in which each frame 200A, 200B, . . . , 200N includes more than one data band or data window 208 in which a corresponding data pulse 206 communicates a PPM-encoded analog signal. Within a frame 200, the data windows 208 are separated from each other, and from the synchronization signals by guardbands 210, as described above. In one example, data windows 208 are used as separate channels to communicate two different PPM-encoded analog signals (e.g., from two different sensors, such as a pressure sensor and a flow sensor). Alternatively, data windows 208 are both used to communicate the same PPM-encoded analog signal. In one further embodiment, each frame includes four data windows 208, however, even more data windows may be possible.

FIG. 3 illustrates first frame 200A at the shorter frame length 201C and the second frame 200B at the nominal frame length 201A. This represents the case where the digital signal being communicated was in a "1" state in a frame that preceded first frame 200A, is in a "0" state during first frame 200A, and which remains in the "0" state during second frame 200B.

In one suitable example, but not by way of limitation, each frame includes two data windows 208. In this example, controller 112 includes a 32.768 kHz crystal oscillator clock circuit in addition to its digital sequencer. Modulation of the length of frame 200 to communicate the digital signal includes either shortening or lengthening the length of frame 200 by one clock cycle (e.g., about 30.52 microseconds). Thus, in this example, the nominal frame length 201A is about 1587 microseconds, the longer frame length 201B is about 1617 microseconds, the shorter frame length 201C is about 1556 microseconds, the synchronization interval is about 183 microseconds, the guardbands are about 213 microseconds, and the data windows are about 366 microseconds.

Figure 4:
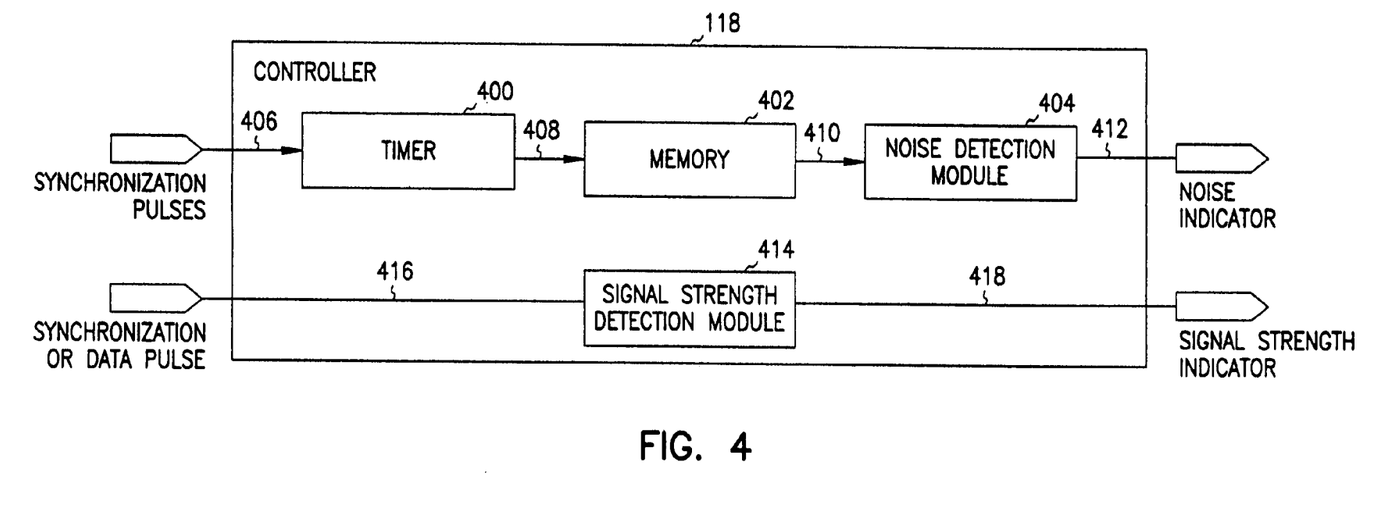
FIG. 4 is a block diagram illustrating portions of an example controller including components for evaluating whether the communication link between transceivers manifests noise exceeding a predetermined level.

FIG. 4 is a block diagram illustrating portions of an example controller 118 including components for evaluating whether the communication link between transceivers 110 and 116 manifests noise exceeding a predetermined level. In this example, controller 118 includes a timer circuit 400, a memory circuit 402 and a noise detection module 404. Timer 400 includes an input, at node/bus 406, that receives an indication of the synchronization pulses 202A-B, 204A-B, etc. as illustrated in FIG. 2. Timer 400 measures the duration value of the corresponding synchronization intervals 202C, 204C, etc., which are output at node/bus 408 for storage in memory 402. After a predetermined number of synchronization interval values are stored in memory 402 over a corresponding plurality of consecutive or nonconsecutive data frames 200, they are output, at node/bus 410, to be processed by noise detection module 404. Noise detection module 404 includes a sequencer-executed sequence of operations that evaluate a characteristic (e.g., variance, standard deviation, distribution characteristic, frequency content, etc.) of the variability of the synchronization interval values.

In one example, the variability characteristic is compared to a predetermined threshold value. If the variability in the duration of the synchronization intervals exceeds the threshold value, a noise indicator value of "1" is output at node 412, otherwise a value of "0" is output. Thus, in this example, the binary noise indicator represents the validity of the analog data being communicated between transceivers 110 and 116. In another example, the variability characteristic itself, which takes on more than two states, is used as a figure of merit of the quality of the analog data being communicated between transceivers 110 and 116. In this manner, the variability characteristic itself may be used in subsequent processing of the transmitted analog data. For example, a larger jitter between synchronization pulses leads to a larger variability characteristic, which may trigger a longer averaging of the analog signal being transmitted to compensate for the increased noise. In this manner, controller 118 may include noise detection components for determining the integrity of the analog data being communicated between transceivers 110 and 116. Among other things, this information may be used to reject transmitted analog data, to qualify transmitted analog data, to ascertain or mark a range of error associated with transmitted analog data, or to compensate for error associated with transmitted analog data.

In one example, as illustrated in FIG. 4, controller 118 also includes a signal strength detection module 414, having an input at node 416 that receives at least one synchronization pulse 202A-B and/or data pulse 206, and having an output at node 418 that provides a responsive indication of signal strength. In one example, signal strength detection module 414 includes an amplitude detector, such as a peak or level detector and associated comparator, for determining the amplitude of the received synchronization or data pulse. In one example, signal strength detection module 414 provides a binary output indication of whether the received signal amplitude exceeds a predetermined threshold level. In another example, signal strength detection module provides a further indication of the actual amplitude value of the received signal (for example, by encoding the amplitude-based signal strength measurement as a variable pulsewidth output pulse for further processing). In this manner, controller 118 may include signal strength detection components for determining the integrity of the data being communicated between transceivers 110 and 116. Among other things, this information may be used to reject or qualify transmitted data. Moreover, the signal strength information may be combined with the noise data provided by noise detection module 404 to provide a combined figure of merit of the received signal. Where the noise and signal strength are both binary indicators, the combined figure of merit may also be a binary indicator based on logic applied to the binary inputs. Where the noise and signal strength are multivalued, the combined figure of merit may also be multivalued, and may differently and independently weight the signal strength and noise information.

Although the above examples have highlighted, for brevity, data transmission by device 102 for reception by remote device 104, it is understood that the above-described communication protocol is also applicable for data transmission by remote device 104 to device 102.

Figure 5:
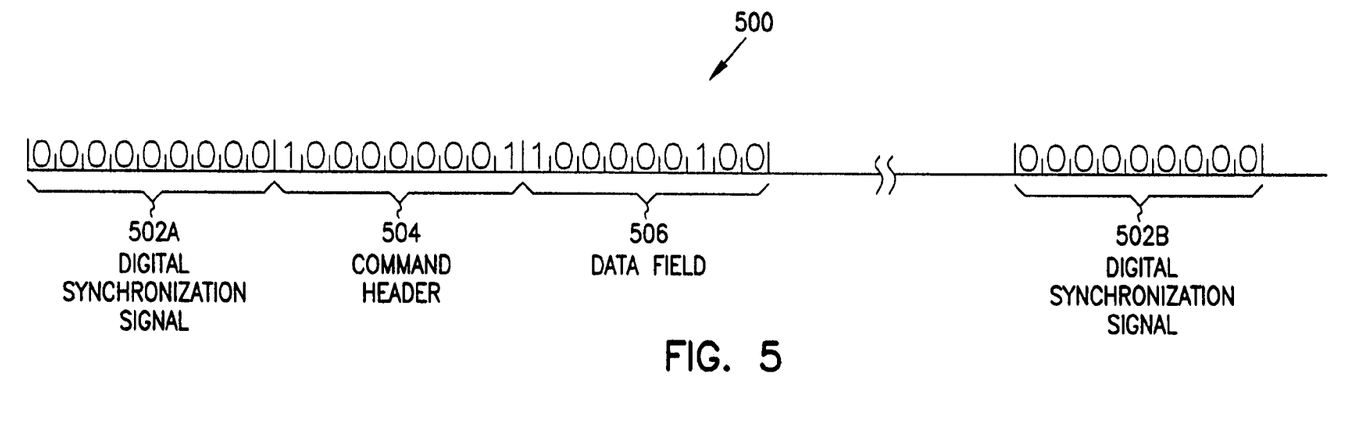
FIG. 5 is a digital signal graph that illustrates generally an example of a bitstream being transmitted from a device (by modulating frame length over successive frames) to another device according to one example of a higher-level protocol.

In a further example, this communication protocol also includes a higher level protocol for further defining transception of the digital data, over a plurality of frames 200, by modulating the length of the frame 200. FIG. 5 is a digital signal graph that illustrates generally an example of a bitstream 500 being transmitted from device 104 (by modulating frame length over successive frames 200) to device 102 according to one example of such a higher-level protocol. In this example, bitstream 500 includes a first digital synchronization signal 502A, a command header 504, one or more optional data field 506, and a subsequent second digital synchronization signal 502B. Digital synchronization signal 502A includes a predetermined sequence of bits (such as, in this example, nine successive zeros) that is recognized by device 102 as initiating a data transmission session from device 104 to device 102. This synchronizes device 102 for receiving and recognizing a following sequence of bits (such as, in this example, nine successive bits) as command header 504. After command header 504 is transmitted, the data transmission session may (but need not) include one or more additional data fields 506 (in this example, data field 506 includes 9 bits, i.e., a "1" start bit followed by eight data bits). The number of data fields 506 (if any) that follow command header 504 is typically defined by information included within command header 504. FIG. 5 also illustrates an example of a second digital synchronization signal 502B initiating a second data transmission session from device 104 to device 102.

Figure 6:
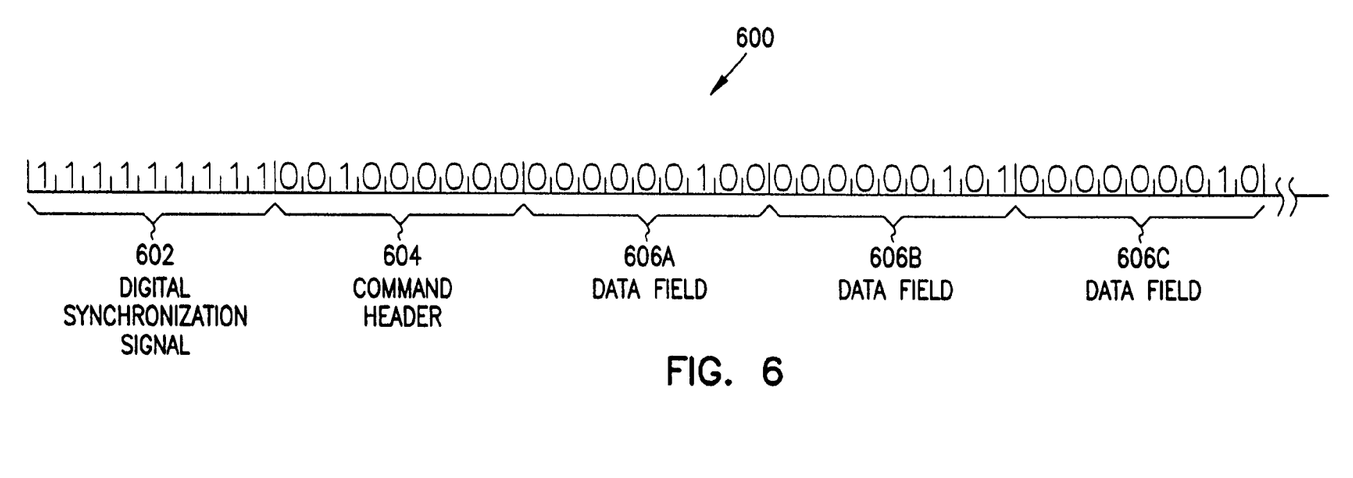
FIG. 6 is a digital signal graph that illustrates generally an example of a bitstream being transmitted from a device (by modulating frame length over successive frames) to another device according to this same example of a higher-level communication protocol.

FIG. 6 is a digital signal graph that illustrates generally an example of a bitstream 600 being transmitted from device 102 (by modulating frame length over successive frames) to device 104 according to this same example of a higher-level communication protocol. In this example, bitstream 600 includes a digital synchronization signal 602, a command header 604, and one or more optional data fields 606A-C. Digital synchronization signal 602 includes a predetermined sequence of bits (such as, in this example, nine successive ones) that is recognized by device 104 as initiating a data transmission session from device 102 to device 104. This synchronizes device 104 for receiving and-recognizing a following sequence of bits (such as, in this example, nine successive bits) as command header 604. After command header 604 is transmitted, the data transmission session may (but need not) include one or more additional data fields 606A-C (in this example, each data field 606 includes 9 bits, i.e., a "0" start bit followed by eight data bits). The number of data fields 606 (if any) that follow command header 604 is typically defined by information included within command header 604.

Figure 7:
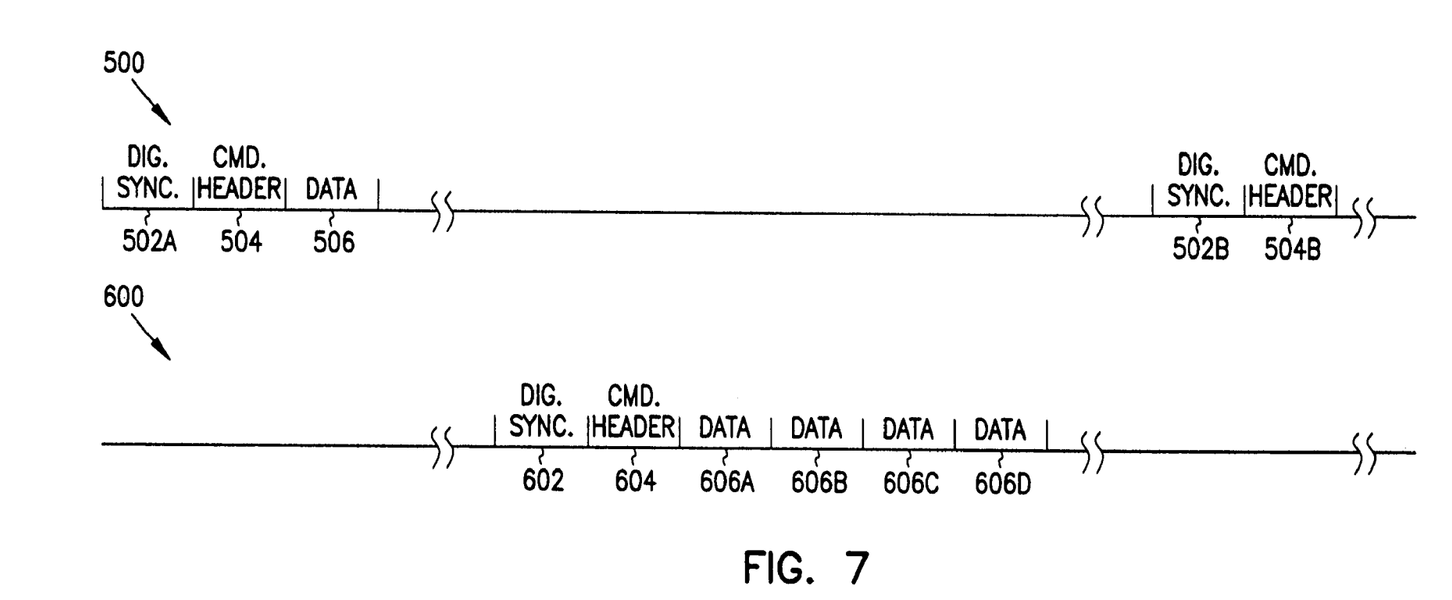
FIG. 7 illustrates generally an example of bidirectional communication between devices.

FIG. 7 illustrates generally an example of bidirectional communication between devices 102 and 104. In this example, device 104 first transmits to device 102 via bitstream 500. After this communication session is completed, then device 102 transmits data to device 104 via bitstream 600. After this second communication session is completed, then device 102 again transmits data to device 104 via bitstream 500 in a third communication session.

Table 1 illustrates one example of how command header 504 is defined for transmitting commands including system control information from device 104 to device 102, such as for configuring an operational mode, requesting return data from device 102, or reading or writing identification information to or from the particular device 102.

TABLE 1

Example Definition of Command Header 504

| Command Bits (8 76543210) | Definition |
| --- | --- |
| 1 00000000 | No Operation |
| 1 00000001 | Mode 1 |
| 1 00000010 | Mode 2 |
| 1 00000011 | Mode 3 |
| 1 00000100 | Mode 4 |
| 1 00000101 | Mode 5 |
| 1 00000111 | Mode 7 |
| 1 01000100 | EEPROM Command: 4 Data Fields 506 Follow |
| 1 01000101 | EEPROM Command: 1 Data Field 506 Follows |
| 1 01000110 | EEPROM Command: 2 Data Fields 506 Follow |
| 1 01000011 | EEPROM Command: 3 Data Fields 506 Follow |
| 1 00001000 | Mode 8 |
| 1 01001010 | EEPROM Write Enable |
| 1 01010100 | EEPROM Write |
| 1 10000001 | Write Scan Select Address |
| 1 10000101 | Scan Read (Response Requested) |
| 1 10001100 | Scan Write (Response Requested) |

Thus, Table 1 illustrates one example of how command header 504 is used to configure controller 112 and/or another component of device 102 into one of several possible modes of operation, to interface with an EEPROM or other memory included within or coupled to controller 112, and/or to interface with one or more scannable registers in memory associated with controller 112.

Table 2 illustrates one example of how command header 604 is defined for transmitting commands from device 102 to device 104, such as for identifying the nature of one or more following data fields.

TABLE 2

Example Definition of Command Header 604

| Command Bits (8 76543210) | Definition |
| --- | --- |
| 0 00000000 | No Operation |
| 0 001xxxmm | Registers 1-4 Data Fields 606 Follows (mm = mode bits) |
| 0 010xxxmm | Registers 5-8 Data Fields 606 Follow (mm = mode bits) |
| 0 011ccccc | 4 EEPROM Data Fields 606 Follow (cccccc = packet counter value) |
| 0 100xxxxx | 4 Scan Data Fields 606 Follow |

Thus, Table 2 illustrates one example of how command header 604 is used to identify subsequently transmitted data field(s) 606, data from the EEPROM or other memory 126 in device 102, or data from scan-chain configured memory registers in device 102.

It is to be understood that the above description is intended to be illustrative, and not restrictive. For example, the above-discussed embodiments may be used in combination with each other. Many other embodiments will be apparent to those of skill in the art upon reviewing the above description. For example, although the data transmission protocol discussed herein has been illustrated in terms of wireless communication techniques, the protocol could also be implemented with a wired electrical or optical connection between transceivers. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A system, comprising:
a transceiver circuit to transceive signals representing at least a first analog signal and a digital signal;
a controller circuit, coupled to the transceiver circuit, to deliver at least one control signal thereto, the controller circuit including executable instructions defining a data frame for communication of the first analog signal and the digital signal, endpoints of the data frame defined by portions of successive first and second synchronization signals and defining a corresponding frame interval, the data frame including a first data band for transceiving a first data pulse therein, a relative position in time of the first data pulse representing the first analog signal, and a modulation of the frame interval representing the digital signal; and
an analog signal interface circuit, coupled to the transceiver circuit, to provide at least the first analog signal representative of acquired data.

2. The system of claim 1, in which the analog signal interface includes at least one sensor.

3. The system of claim 2, in which the sensor includes at least one of: a biopotential sensor, a biofluid pressure sensor, a bio fluid flow sensor, a temperature sensor, a pH sensor, an impedance sensor, an oxygen sensor, and an electrochemical sensor.

4. The system of claim 1, in which the first and second synchronization signals each include first and second synchronization pulses defining endpoints of the first and second synchronization signals.

5. The system of claim 4, further comprising:
a timer circuit to measure a duration of a synchronization interval defined by the first and second synchronization pulses; and
a noise detection module, coupled to the timer, to determine the presence of noise based on a variability of the duration of a plurality of the synchronization intervals.

6. The system of claim 1, in which the first data band is separated from the first and second synchronization signals by at least a first guard band that is longer than the first and second synchronization intervals.

7. The system of claim 1, in which the modulating frame interval includes different first, second, and third frame interval values.

8. The system of claim 7, in which the modulating frame interval represents a state of the digital signal during a present frame relative to the state during a previous frame.

9. The system of claim 7, in which the modulating frame interval corresponds to:
the first frame interval value, if the state of the digital signal during the present frame is unchanged from the previous frame;
the second frame interval value, if the state of the digital signal changed from a first state value during the previous frame to a second state value during the present frame; and the third frame interval value, if the state of the digital signal changed from the second state value during the previous frame to the first state value during the present frame.

10. The system of claim 1, the data frame further comprising at least a second data band for transceiving a second data pulse therein, a relative position in time of the second data pulse representing a second analog signal.

11. The system of claim 10, in which:
the first data band is separated from the first and second synchronization signals by at least a first guard band that is longer than the first and second synchronization signals;
the second data band is separated from the first and second synchronization signals by at least a second guard band that is longer than the first and second synchronization signals; and
the first and second data bands are separated by at least a third guard band that is longer than the first and second synchronization signals.

12. The system of claim 1, in which the modulating frame interval includes a digital synchronization command.

13. The system of claim 12, in which the digital synchronization command includes a predetermined start bit followed by a predetermined sequence of following bits.

14. The system of claim 12, in which the modulating frame interval includes a header after the digital synchronization command.

15. The system of claim 14, in which the header includes a predetermined start bit followed by a predetermined sequence of following bits.

16. The system of claim 14, in which the header includes system control information.

17. The system of claim 1, further comprising a memory device including digital data represented in the digital signal.

18. The system of claim 1, further comprising a signal strength detection module, coupled to the transceiver to receive at least one of a synchronization pulse and a data pulse, the signal strength detection module including an output providing an indication of the amplitude of the received one of the synchronization pulse and the data pulse.

19. The system of claim 18, in which the signal strength detection module includes at least one of a peak detector and a level detector, coupled to the transceiver.

20. The system of claim 1, in which the transceiver circuit is configured to communicate a pulse selected from a radio-frequency (RF) pulse, a magnetic field coupling pulse, an electric field coupling pulse, an ultrasound pulse, a pressure pulse, a thermal pulse, an infrared (IR) pulse, a light pulse, an electromagnetic pulse, and a tissue conduction pulse.

21. A system, comprising:
a transceiver circuit to transceive signals representing at least a first analog signal and a digital signal;
a controller circuit, coupled to the transceiver circuit, to deliver at least one control signal thereto, the controller circuit including executable instructions defining a data frame for communication of the first analog signal and the digital signal, endpoints of the data frame defined by portions of successive first and second synchronization signals and defining a corresponding frame interval, the data frame including a first data band for transceiving a first data pulse therein, a relative position in time of the first data pulse representing the first analog signal, and a modulation of the frame interval representing the digital signal, wherein the first and second synchronization signals each include first and second synchronization pulses defining endpoints of the first and second synchronization signals;
a timer circuit to measure a duration of a synchronization interval defined by the first and second synchronization pulses; and
a noise detection module, coupled to the timer, to determine the presence of noise based on a variability of the duration of a plurality of the synchronization intervals.

* * * * *

UNITED STATES PATENT AND TRADEMARK OFFICE
CERTIFICATE OF CORRECTION

PATENT NO.       : 7,418,297 B2                                    Page 1 of 1
APPLICATION NO.  : 11/193818
DATED            : August 26, 2008
INVENTOR(S)      : Reid Bornhoft et al.

It is certified that error appears in the above-identified patent and that said Letters Patent is hereby corrected as shown below:

Column 9, line 30 (claim 15), replace "predetennined" with --predetermined--.

Signed and Sealed this

Twenty-third Day of June, 2009

JOHN DOLL
*Acting Director of the United States Patent and Trademark Office*